(12) United States Patent
Bucholz (10) Patent No.: US 6,405,556 B1
(45) Date of Patent: Jun. 18, 2002

(54) INSULATED CONTAINER

(76) Inventor: Frederick S. Bucholz, 1649 No. 264$^{st}$, Waterloo, NE (US) 68069

( * ) Notice: Subject to any disclaimer, the term of this patent is extended or adjusted under 35 U.S.C. 154(b) by 0 days.

(21) Appl. No.: 09/698,583

(22) Filed: Oct. 27, 2000

(51) Int. Cl.$^7$ .............................. F25D 3/08; F25B 29/00
(52) U.S. Cl. ..................... 62/457.2; 62/371; 165/201
(58) Field of Search ............................ 62/457.1, 457.2, 62/371, 372, 45.1; 165/201

(56) References Cited

U.S. PATENT DOCUMENTS

| | | | |
|---|---|---|---|
| 4,377,077 A | * | 3/1983 | Granlund .................... 62/457.1 |
| 4,509,587 A | * | 4/1985 | Clark et al. .................... 165/61 |
| 4,530,816 A | * | 7/1985 | Douglas-Hamilton .......... 422/1 |
| 5,355,684 A | * | 10/1994 | Guice .......................... 62/54.2 |
| 5,397,010 A | * | 3/1995 | Gibot .......................... 220/1.5 |
| 5,405,012 A | * | 4/1995 | Shindler et al. ............. 206/569 |
| 5,417,082 A | * | 5/1995 | Foster et al. ............... 62/457.1 |
| 5,419,152 A | * | 5/1995 | Silber .......................... 62/372 |
| 5,850,917 A | * | 12/1998 | Denton et al. ............... 206/366 |
| 5,983,661 A | * | 11/1999 | Wiesman ................... 62/457.1 |

* cited by examiner

*Primary Examiner*—William C. Doerrler
(74) *Attorney, Agent, or Firm*—Michael Best & Friedrich LLC (57) ABSTRACT

The present invention provides an insulated container that is especially useful in cooling and transporting thermally sensitive materials such as pharmaceuticals, organs, tissues and vaccines. In general, the present invention comprises a container having a base unit and a lid. The container is insulated, preferably through the use of vacuum insulation paneling.

A tray holding specimens is placed within the insulated container along with a coolant. To affect the rate at which the coolant draws heat from the specimen within the tray, another competing heat source is placed within the container along with the specimen and coolant. In the preferred embodiment, the competing heat source comprises expanded polystyrene panels coating the inner surface of the insulated container.

26 Claims, 7 Drawing Sheets

INSULATED CONTAINER

FIELD OF THE INVENTION

This invention relates generally to insulated containers and, more particularly, to a shipping container that is especially useful in cooling and transporting thermally sensitive materials such as pharmaceuticals, organs, tissues and vaccines.

BACKGROUND OF THE INVENTION

It is often desirable and necessary to cool or freeze a specimen in order to preserve it for storage or transport. However, a number of specimens are sensitive to, and can be damaged by, changes in temperature and freezing. The specimens contemplated for use with the present invention can be any material which it is desirable to protect and thermally insulate during transport. Examples of such specimens can be chemicals, organs, tissues, blood, vaccines, food products, or other such materials.

For example, freezing a specimen of equine (horse) semen for storage or shipment appears to damage the spermatozoa therein. As a result, the pregnancy rates achieved using frozen (and then thawed) equine semen is a relatively low 50–60 percent. In contrast, the pregnancy rates achieved using horse semen that has been cooled, but not frozen, can be 90 percent or higher.

And although cooling equine semen is more effective than freezing it, cooling can also result in damage to a specimen. If an equine semen specimen is cooled too rapidly, thermal shock can cause irreversible damage to the spermatozoa. On the other hand, if the specimen is cooled too slowly, the spermatozoa will be damaged by the prolonged exposure to high temperatures.

Accordingly, because the viability of a specimen (such as equine semen) can be affected by the rate at which it is cooled, there is a need for a storage and/or shipping device that can be used to cool a specimen at a controlled and consistent rate. In addition, once the specimen's target temperature has been reached, the device should be able to maintain the specimen within a desired temperature range for extended periods of time, regardless of the ambient temperature outside the device.

SUMMARY OF THE INVENTION

In general, the present invention fulfills these needs by providing a device comprising an container having a base unit and a lid. The container is insulated, preferably through the use of vacuum insulation paneling.

A tray adapted to hold specimen jars or syringes is placed within the insulated container along with a coolant. To control the rate at which the coolant draws heat from the specimen, one or more competing heat sources are placed within the container along with the specimen and coolant. In the preferred embodiment, the competing heat source comprises expanded polystyrene panels coating the inner surface of the insulated container.

DETAILED DESCRIPTION OF THE INVENTION

Figure 1:
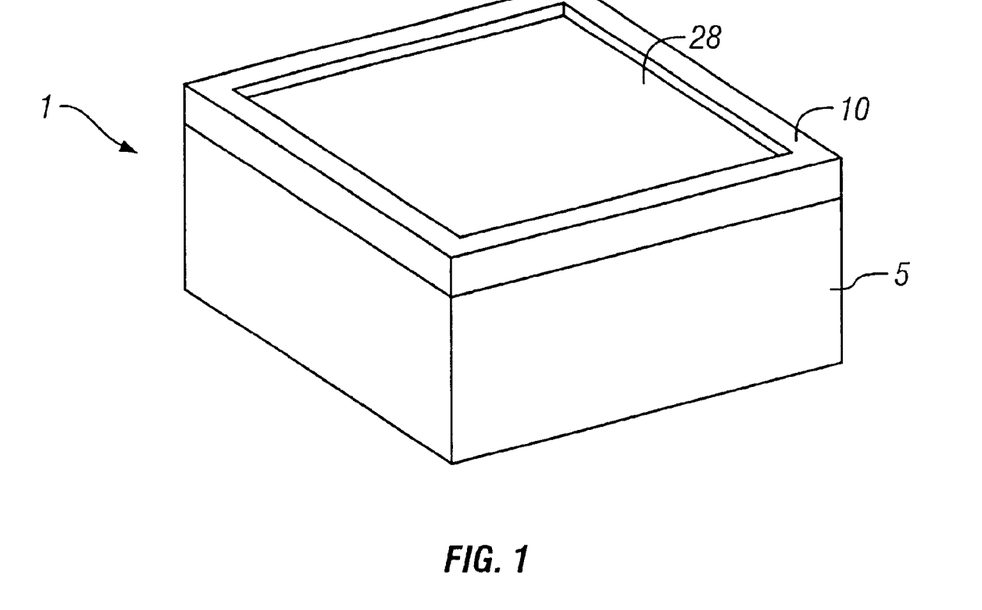
FIG. 1 is a perspective view of an embodiment of the inventive container.
Figure 2:
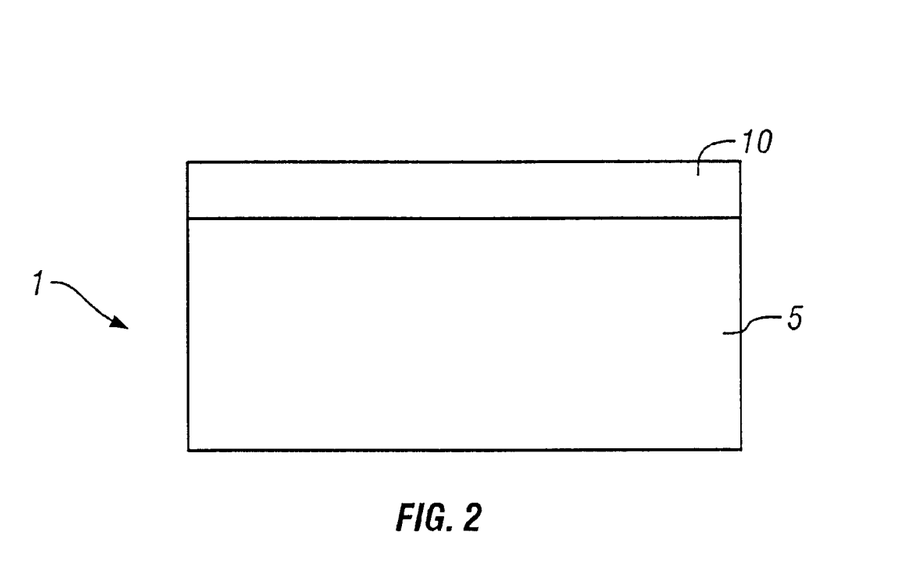
FIG. 2 is a side view of the embodiment of FIG. 1.
Figure 3:
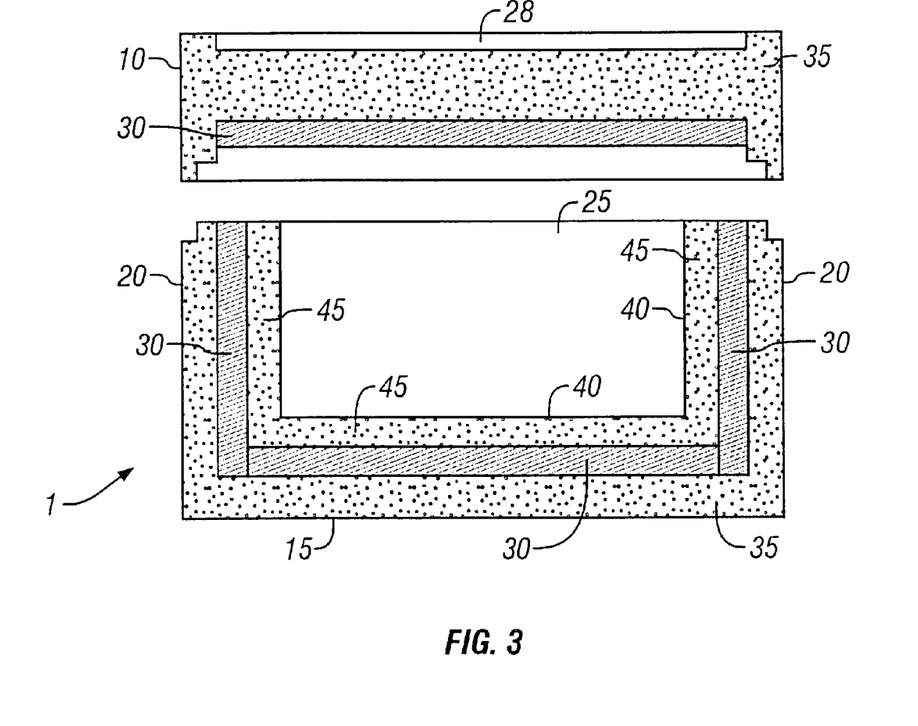
FIG. 3 is a cross-sectional side view of the embodiment of FIG. 1 taken along line III—III.
Figure 4:
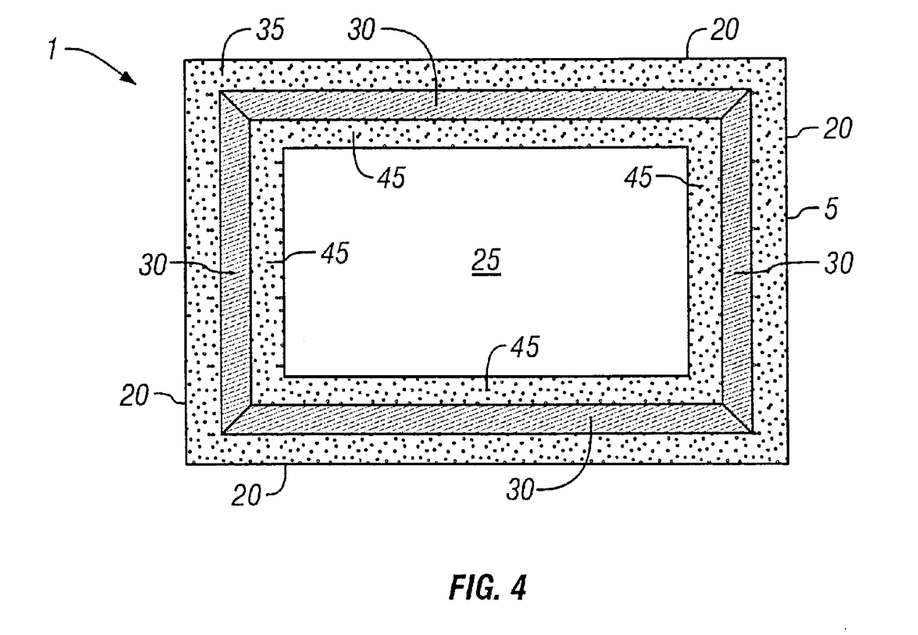
FIG. 4 is a cross-sectional top view of the embodiment of FIG. 1 taken along line IV—IV.

As shown in FIGS. 1–6, one embodiment of the present invention is a container 1 comprising a base 5 and a lid 10. In the embodiment shown in FIGS. 1–6, container 1 is a cube-shaped box and base 5 has a bottom wall 15 and side walls 20. As best seen in FIGS. 3 and 4, lid 10, bottom wall 15 and side walls 20 define a payload area 25 wherein one or more specimens and a coolant can be stored. In the preferred embodiment shown in FIGS. 1–6, the dimensions of container 1 are 11"×14.25"×8.25", and the dimensions of the payload area are 7"×10.25"×4.5". It is also preferred that the top surface of the lid define an indentation 28 for holding documentation concerning the specimen stored within the container.

Figure 13:
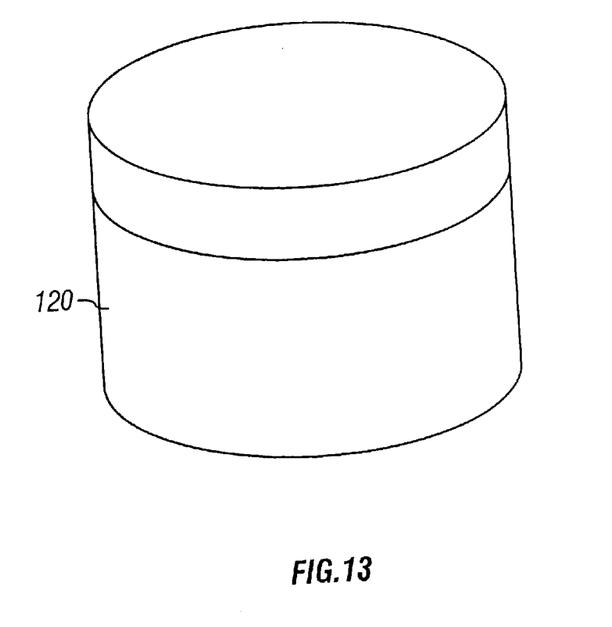
FIG. 13 is a perspective view of another embodiment of the present invention.
Figure 14:
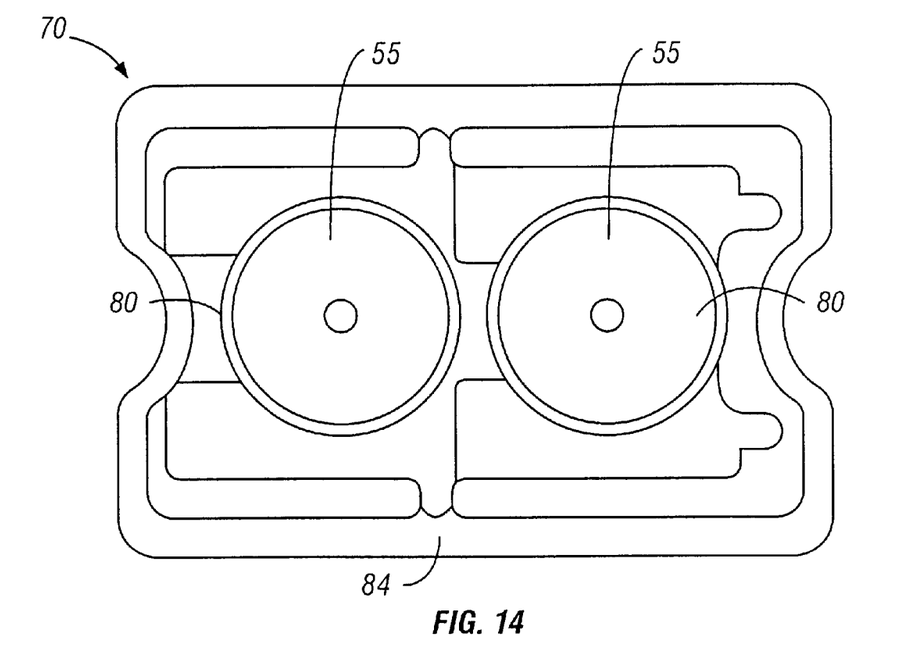
FIG. 14 is a top plane view of the bottom half of the tray of FIG. 7 with two specimen jars stored therein.
Figure 15:
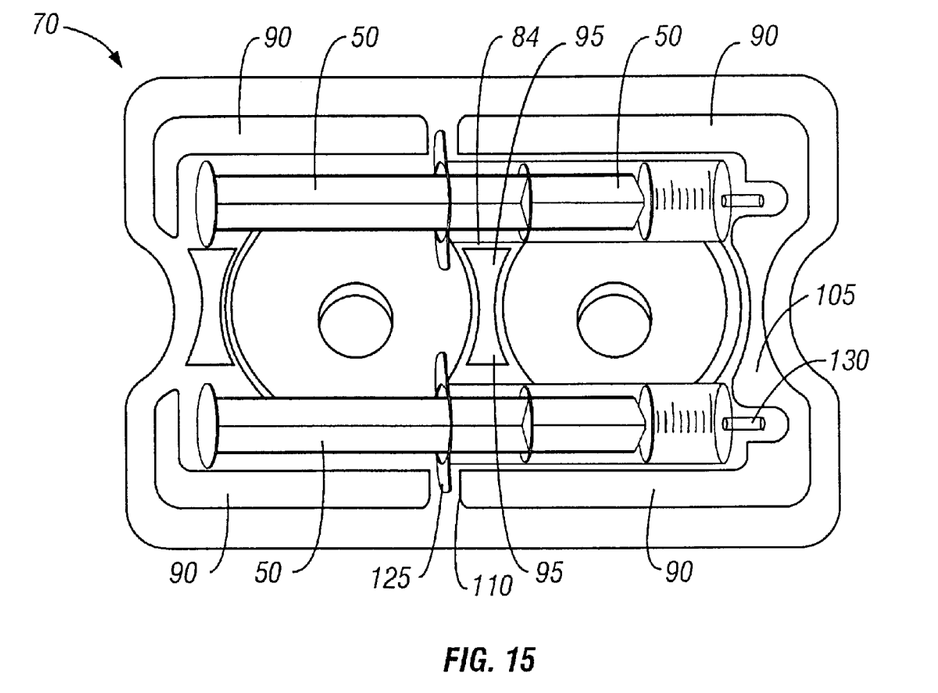
FIG. 15 is a top plane view of the bottom half of the tray of FIG. 7 with two specimen syringes stored therein.

It should be understood that the embodiment shown in FIGS. 1–6 is merely an illustrative example of the present invention, and that a container of any type, shape and size can be used. For example, the container could be cylinder-shaped, such as the container 120 shown in FIG. 13.

Container 1 is insulated to at least partially thermally insulate the contents of the container from the ambient temperature outside of the container. In the embodiment shown in FIGS. 1–6, container 1 is insulated by the use of vacuum insulation panels 30 in lid 10, bottom wall 15 and side walls 20. Vacuum insulation panels are well known in the art and are evacuated envelopes surrounding microporous cores having low thermal conductivity. When pressure within the core is reduced enough, the pore divisions significantly interfere with heat transfer through any remaining air, resulting in insulation resistance (R) values of 20–40 per inch. Vacuum insulation panels such as those featured in the preferred embodiment described herein are available from Advantek, Inc. of Minneapolis, Minn.

In the preferred embodiment shown in FIGS. 3–4, the vacuum insulation panels 30 are one half inch thick. However, other thicknesses can also be used, depending on the degree of insulation desired. And although vacuum insulation panels are the preferred insulating means for the present invention, other insulators—such as polyurethane or Styrofoam—can also be used.

Although not necessary for the present invention, in the preferred embodiment, container 1 features a protective shell 35. As best seen in FIGS. 3–4, protective shell 35 covers the outer surface of vacuum insulation panels 30 to protect the panels from damage that may occur during shipping or other use of the container. In the embodiment shown in FIGS. 3–4, the protective shell is made from expanded polystyrene. However, any suitable material may be used.

Figure 5:
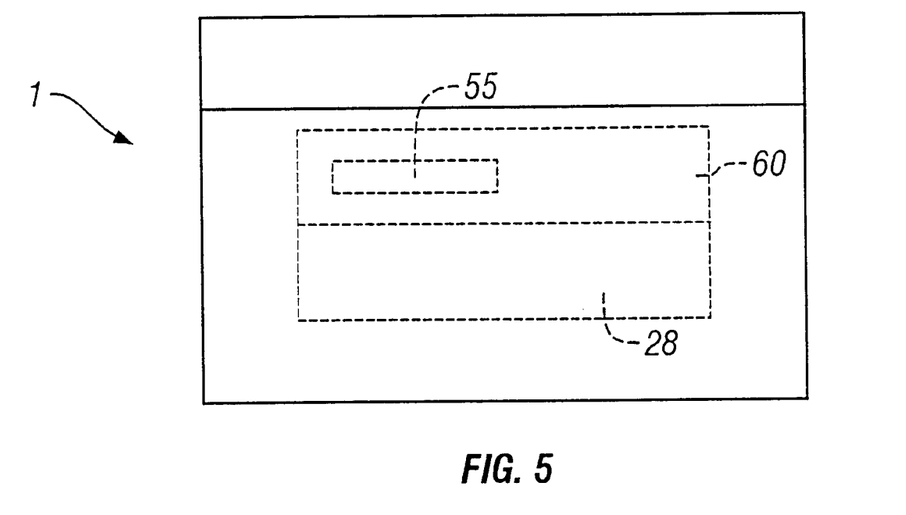
FIG. 5 is a front view of the embodiment of FIG. 1 with dotted lines showing the position of a coolant, tray and cylindrical jar placed therein.
Figure 6:
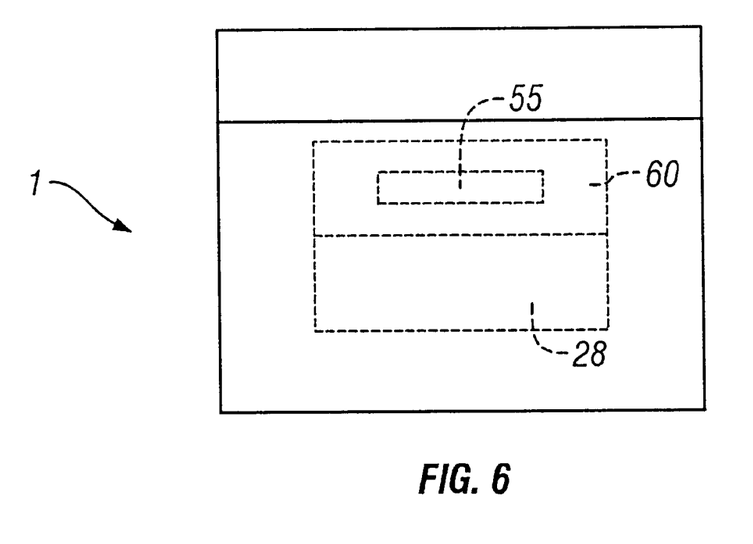
FIG. 6 is a side view of the embodiment of FIG. 1 with dotted lines showing the position of a coolant, tray and cylindrical jar placed therein.
Figure 7:
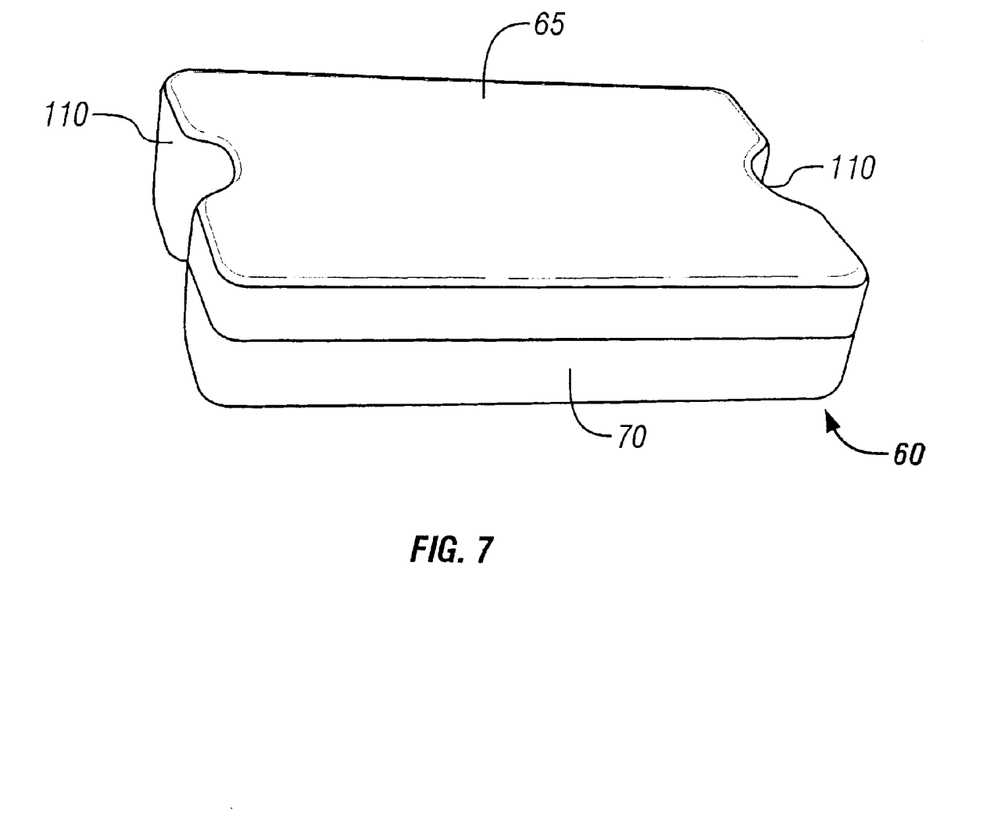
FIG. 7 is perspective view of the tray of FIGS. 5 and 6.
Figure 8:
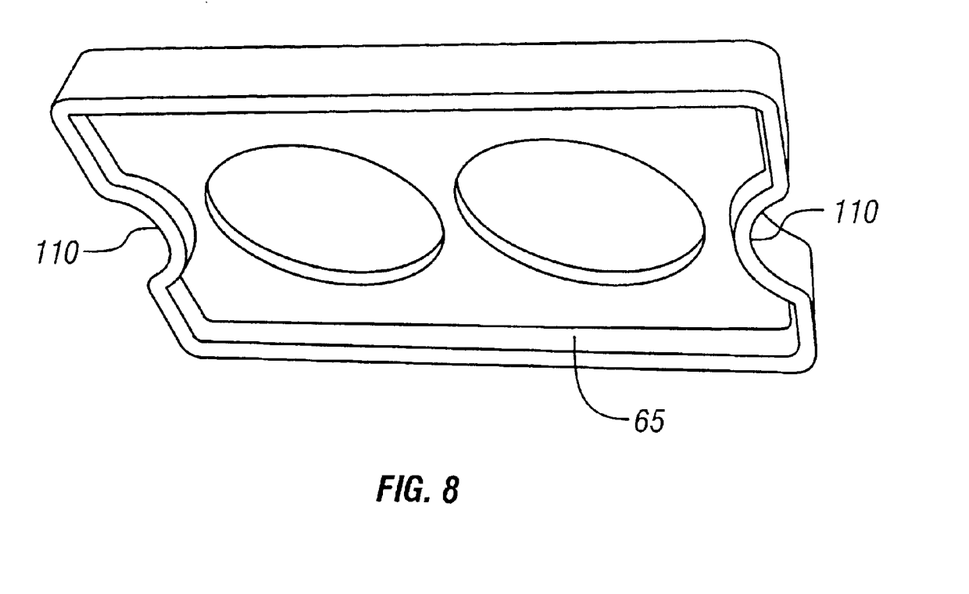
FIG. 8 is a perspective view of the bottom surface of the top half of the tray of FIG. 7.

To cool a specimen, it is placed within container 1 with a coolant 28. A specimen can be placed and held in the container 1 in a variety of different ways. Typically, an equine semen specimen is carried in either a syringe 50 (see FIG. 11) or a cylindrical jar 55 (see FIG. 12), and the syringe 50 or cylinder jar 55 is then secured within container 1. If held in a cylindrical jar 55, the semen is typically placed first in a plastic bag that is then inserted into the cylindrical jar 55 along with a material such as cotton to act as an absorbent and cushion. In the preferred embodiment, syringe 50 or cylindrical jar 55 is secured within a tray 60, which is then placed within container 1 on top of coolant 28 as shown in FIGS. 5–6.

In the preferred embodiment shown in FIGS. 7–10, tray 60 comprises a top half 65 and a bottom half 70. Preferably, tray 60 is made from expanded polystyrene and dimensioned to fit snugly within the top half of payload area of container 1 atop coolant 28 (as shown in FIGS. 5–6), i.e. approximately 7"×10.25"×2.5". However, the tray can be any suitable size and made from any suitable material. It is also preferable that tray 60 feature side concavities 110, thereby providing areas where the tray can be easily gripped when it is being placed in or removed from container 1. Holes 115 are provided in the bottom half 70 to provide open communication between the coolant 28 and the specimen(s) stored within tray 60.

Figure 9:
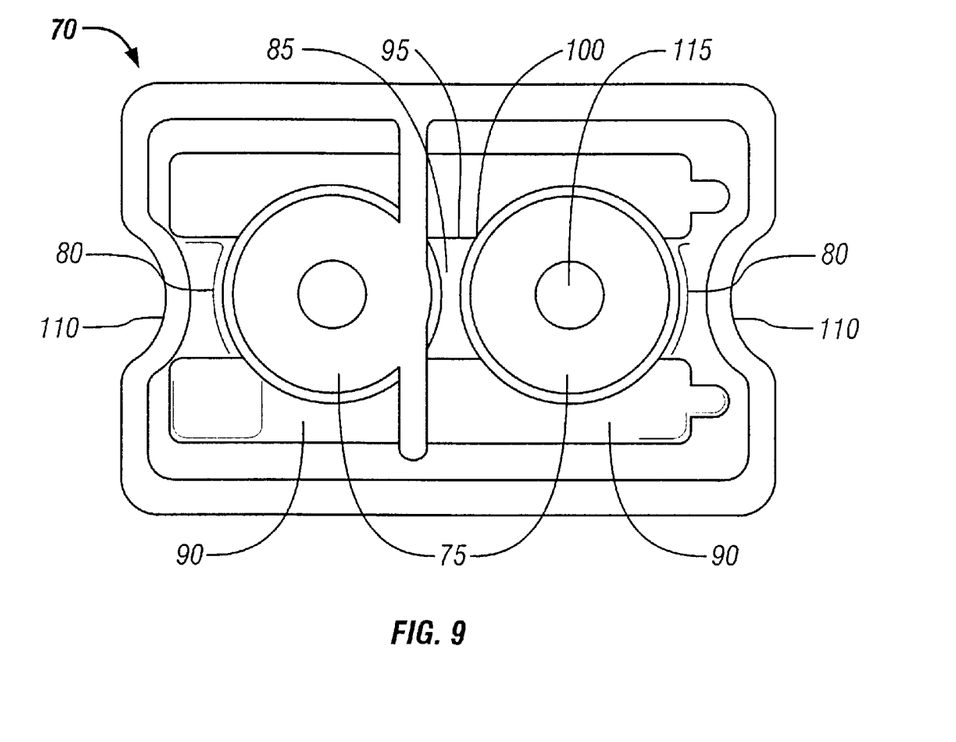
FIG. 9 is a top plane view of the bottom half of the tray of FIG. 7.
Figure 10:
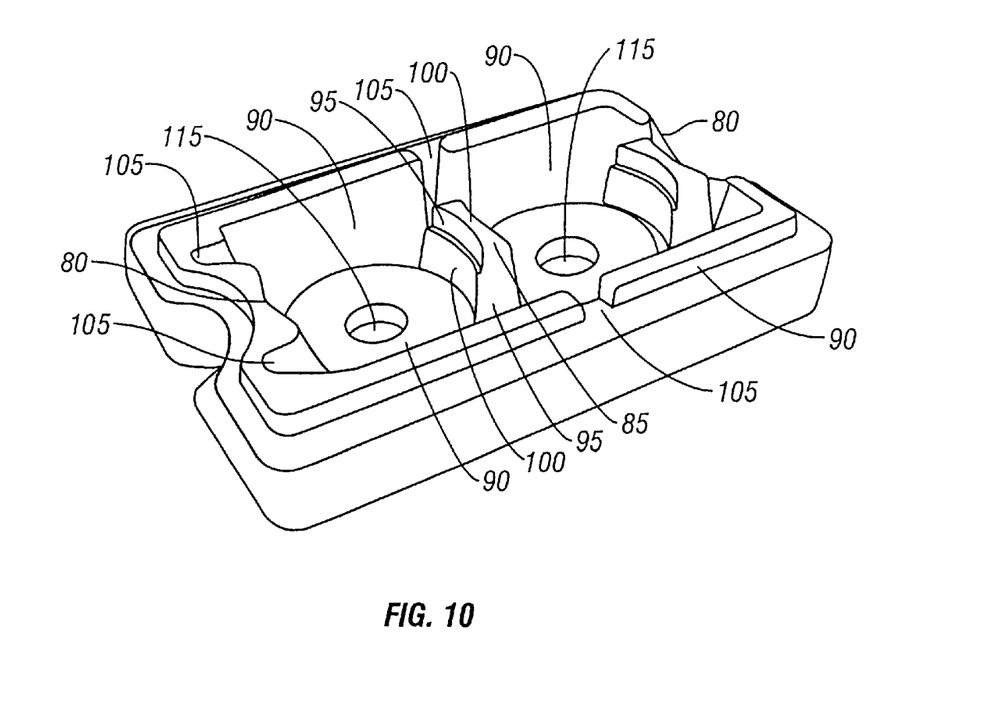
FIG. 10 is a perspective view of the bottom half of the tray of FIG. 7.

Preferably, the tray bottom 70 defines a holding area 75 that can accommodate two syringes or two cylindrical jars. As best seen in FIGS. 9 and 10, holding area 75 is defined by curved side wall 80, straight side walls 90, and middle wall segment 85 having end faces 95 and curved side faces 100.

Figure 11:
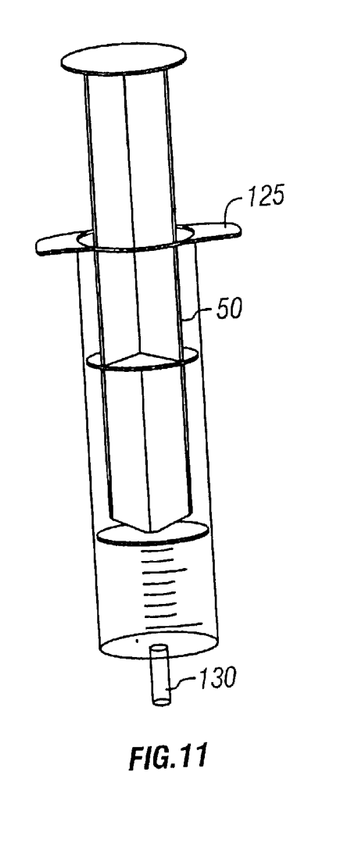
FIG. 11 is a perspective view of a specimen syringe.

To store a cylindrical jar in the holding area 75, the cylindrical jar is placed in between one of the curved side walls 80 and the curved side face 100 opposite said curved side wall 80. Curved side wall 80 and middle wall segment 84 are sized and shaped to engage a cylindrical jar 55 placed between them. FIG. 11 shows two cylindrical jars 55 stored within tray bottom 70 and held in place by curved side walls 80 and middle wall segment 84.

Figure 12:
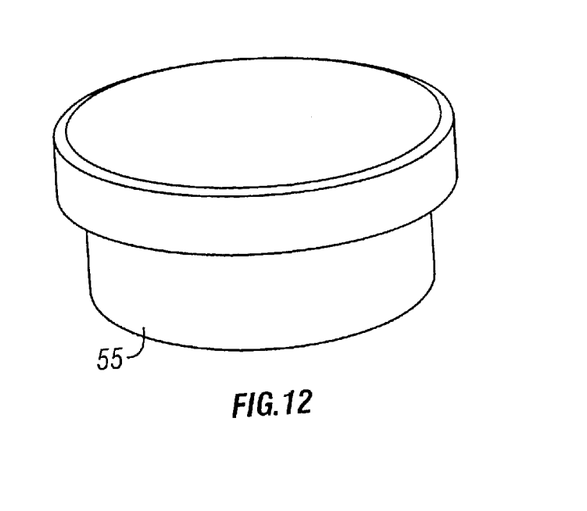
FIG. 12 is a perspective view of a specimen jar.

To store a syringe 50 in the holding area 75, the syringe is placed along one of the straight side walls 90 as shown in FIG. 12. The syringe is held in place by the selected straight side wall 90 and the end face 95 opposite said straight side wall. In the preferred embodiment, an end notch 105 is provided in curved side wall 80 to accommodate and hold the end 130 of the syringe. A side notch 110 can also be provided in straight side wall 90 to accommodate and hold syringe skirt 125.

The coolant can be any suitable coolant known in the art, including, but not limited to, ice, gelatinized ice, or chemical coolants. In the preferred embodiment the chemical coolant known as the "Thermal Media Pack," available from Mid-Lands Chemical Co. of Omaha, Nebr., is used. Preferably, the coolant, is placed in the bottom of container 1 and underneath specimen. However, coolant 28 can also be placed above or to the side of the specimen. In addition, depending on the rate and degree of cooling desired, more than one coolant can be placed in the container, in any combination of the positions mentioned herein (for example, two coolants below the specimen, or one above and one below the specimen).

To control the rate at which coolant 28 cools the specimen, another competing heat source 40 is placed within the container 1 with the specimen and coolant 28. For example, the competing heat source can be a thermally active material such as expanded polystyrene. In the preferred embodiment shown in FIGS. 1–4, the competing heat source comprises expanded polystyrene panels 45 placed in container 1 adjacent the inner surface of the vacuum insulation panels 30 in bottom wall 15 and side walls 20.

The amount of expanded polystyrene within the container 1 will affect the rate at which the coolant 28 cools the specimen. The more expanded polystyrene within the container—in other words the larger the competing heat source—the slower the cooling rate. Conversely, if less expanded polystyrene is placed within the container, there is less of a competing heat source and, therefore, the cooling rate is accelerated. Of course, if a tray like that described above is used to store specimens in the container and said tray is made from expanded polystyrene, then the tray will also act as a competing heat source and further slow the cooling rate.

For equine semen, the optimum cooling rate is about 0.5° C./minute from 20° C. to 5° C. For the preferred embodiment described above and shown in FIGS. 1–4, it has been found that this cooling rate can be achieved by using expanded polystyrene panels 45 that are approximately three fourths of an inch thick. These polystyrene panels 45, in combination with the preferred vacuum insulation panels 30 and the preferred tray 60 described above, also result in a container that is able to maintain an equine semen sample at a steady state temperature range of between 4° C. and 10° C. for 100 hours or longer. Of course, different cooling rates and steady state temperatures can be achieved by varying the degree of insulation (such as by varying the thickness of the vacuum insulation panels) and the amount of the competing heat source (such as by varying the thickness of the inner expanded polystyrene panels).

While the present invention is described above in connection with specific embodiments, the invention is intended to cover all alternatives, modifications or equivalents that may be included within its sphere and scope, as defined by the appended claims.

What is claimed is:

1. An apparatus for cooling and storing a specimen comprising:
    an insulated container comprising one or more vacuum insulation panels having inner surfaces defining a cavity for receiving and storing the specimen;
    a coolant located within the cavity and in thermal communication with the specimen stored within the cavity;
    expanded polystyrene located within the cavity and in thermal communication with the coolant for affecting the rate of cooling.

2. The apparatus of claim 1 further comprising means for holding the specimen in the cavity.

3. The apparatus of claim 1 wherein the expanded polystyrene comprises a layer of expanded polystyrene lining at least a portion of the inner surfaces of the vacuum insulation panels.

4. The apparatus of claims 1 or 3 wherein the vacuum insulation panel is about one half inch thick.

5. The apparatus of claim 1 wherein the insulated container comprises a base and a lid.

6. The apparatus of claims 3 or 4 wherein the expanded polystyrene lining is about three fourths of an inch thick.

7. The apparatus of claim 5 wherein the base has an outer surface and further comprising a protective shell about the outer surface of the base.

8. The apparatus of claims 5 or 7 wherein the lid has an outer surface and further comprising a protective shell about the outer surface of the lid.

9. The apparatus of claim 7 wherein the protective shell comprises expanded polystrene.

10. The apparatus of claim 8 wherein the protective shell comprises expanded polystrene.

11. The apparatus of claim 2 wherein the holding means comprises a tray placed within the cavity of the insulated container.

12. The apparatus of claim 1 wherein the insulated container has an insulation resistance value of about 20–40.

13. An apparatus for cooling and storing a specimen comprising:
- an insulated container sized and shaped for storing the specimen and having an inner surface defining a cavity for receiving and storing the specimen;
- a coolant located within the cavity of the insulated container and in thermal communication with the specimen stored within the cavity; and
- a competing heat source located within the cavity and in thermal communication with the coolant for affecting the rate of cooling.

14. The apparatus of claim 13 wherein the insulated container comprises a vacuum insulation panel.

15. The apparatus of claim 14 wherein the insulated container comprises a base and a lid, the base having a bottom and at least one side wall.

16. The apparatus of claim 15 wherein the bottom and side walls comprise vacuum insulation panels.

17. The apparatus of claims 13, 14 or 16 wherein the competing heat source comprises expanded polystrene.

18. The apparatus of claim 13 wherein the insulated container has an outer surface and further comprising a protective shell about the outer surface of the insulated container.

19. The apparatus of claim 13 wherein the insulated container comprises a vacuum insulation panel, the competing heat source comprises expanded polystrene, and the expanded polystrene lines at least a portion of the inner surface of the cavity.

20. The apparatus of claims 13 or 19 further comprising means for holding the specimen in the container.

21. The apparatus of claim 20 wherein the holding means comprises a tray with lid placed within the insulated container.

22. The apparatus of claim 13 wherein the insulated container has an insulation resistance value of about 20–40.

23. The apparatus of claims 13 or 21 wherein the tray defines a holding area sized and shaped to receive any receptacle chosen from the group consisting of a jar, a bag, and a syringe.

24. The apparatus of claim 23 wherein the holding area has a perimeter, the tray has opposing curved side walls and opposing straight side walls defining the perimeter of the holding area, further comprising and middle wall segment located within the perimeter of the holding area and further defining the holding area.

25. The apparatus of claims 11, 21 or 23 wherein the tray comprises expanded polystyrene.

26. The apparatus of claims 1, 3, 4, 13 or 19 wherein the coolant cools the specimen at a rate of about 0.5° C./minute from 20° C. to 5° C.

* * * * *